United States Patent [19]
Msika et al.

[11] Patent Number: 5,939,054
[45] Date of Patent: Aug. 17, 1999

[54] SUNSCREEN COMPOSITIONS COMPRISING A MIXTURE OF TITANIUM AND/OR ZINC OXIDE PARTICLES, METHOD OF PREPARING THE SAME AND USE THEREOF

[75] Inventors: Philippe Msika, Toulouse; Francis Carriere, Castanet-Tolosan; Jean-Pierre Fabre, Castres; France Boyer, Pechabou, all of France

[73] Assignee: Pierre Fabre Dermo-Cosmetique, France

[21] Appl. No.: 08/913,428

[22] PCT Filed: Mar. 14, 1996

[86] PCT No.: PCT/FR96/00393

§ 371 Date: Sep. 15, 1997

§ 102(e) Date: Sep. 15, 1997

[87] PCT Pub. No.: WO96/28136

PCT Pub. Date: Sep. 19, 1996

[30] Foreign Application Priority Data

Mar. 15, 1995 [FR] France .................. 95 02997

[51] Int. Cl.⁶ .............. A61K 7/42; A61K 7/00; C09C 1/04; C09C 1/36
[52] U.S. Cl. ............. 424/59; 106/425; 106/428; 106/436; 252/313.1; 252/315.4
[58] Field of Search ............... 424/59, 60, 400, 424/401; 514/772, 784, 785, 786; 106/436, 425, 428; 252/313.1, 315.4

[56] References Cited

U.S. PATENT DOCUMENTS

| 5,366,660 | 11/1994 | Tapley | 252/309 |
| 5,573,753 | 11/1996 | Tapley | 424/59 |
| 5,605,652 | 2/1997 | Tapley | 252/313.1 |

FOREIGN PATENT DOCUMENTS

| WO 90/11067 | 10/1990 | European Pat. Off. . |
| 0 433 086 A1 | 6/1991 | European Pat. Off. . |
| 0 456 460 A2 | 11/1991 | European Pat. Off. . |
| 0 456 460 A3 | 11/1991 | European Pat. Off. . |
| 0 535 972 A1 | 4/1993 | European Pat. Off. . |
| 2 184 356 | 6/1987 | United Kingdom . |

*Primary Examiner*—Shelley A. Dodson
*Attorney, Agent, or Firm*—Rockey, Milnamow & Katz

[57] ABSTRACT

A sunscreen composition containing a synergic mixture of titanium and/or zinc oxide particles, characterized in that said particles are incorporated in paste-forming oils and/or esters and/or fatty alcohols and/or ethers selected so as to provide a wetting point of the incorporated titanium oxide particles and of the incorporated zinc oxide particles lower than about 5 and a flow point of said incorporatedparticles lower than about 30. The invention also provides a method for preparing said composition and the use thereof for protecting the skin against ultraviolet radiation and for maintaining the monocrystalline dispersion of minerals in the formulation and on the skin.

20 Claims, No Drawings

SUNSCREEN COMPOSITIONS COMPRISING A MIXTURE OF TITANIUM AND/OR ZINC OXIDE PARTICLES, METHOD OF PREPARING THE SAME AND USE THEREOF

The subject of the invention is sunscreen compositions based on titanium oxide and/or on zinc oxide. It is also targeted at a method for producing them and at their cosmetic and therapeutic use in protecting the skin against all the effects of ultraviolet radiation A and B.

It is known to use titanium oxide ($TiO_2$) and/or zinc oxide (ZnO) as agents for reflecting ultraviolet rays.

By way of examples, Patents EP 91 304 100, GB 87/17662 or WO 89/01438 describe sunscreen compositions containing titanium oxide as agent for protecting against radiation.

In the same way, Patents EP 535 972 and WO 92/13517 describe sunscreen compositions containing zinc oxide as agent for protecting against radiation.

Patents FR 2 591 480 and EP 833 086 describe, for their part, sunscreen compositions containing a combination of the two oxides. It appears that this combination has a synergic effect on the value of the sun protection factor. This combination is consequently shown to be particularly advantageous in the production of sunscreen compositions.

However, the compositions thus obtained might be further improved. This is because it would be beneficial to increase their stability and in particular the homogeneity of the particle dispersion. Their protective power might also be further optimized.

The aim of the invention is to provide a sunscreen composition based on titanium oxide and/or on zinc oxide which is better in quality than those already existing as regards:

their stability with time,
  the homogeneity of their dispersion in the formula and on the skin,
  the non-reagglomeration of the crystals with time, and their protective power.

Success has been achieved, according to the invention, by employing zinc oxide particles and/or titanium oxide particles incorporated in paste-forming oils and/or esters and/or fatty alcohols and/or ethers selected with the aim of producing:

a wetting point for the incorporated titanium oxide particles and a wetting point for the incorporated zinc oxide particles which are less than approximately 5,
  a flow point for the incorporated titanium oxide particles and a flow point for the incorporated zinc oxide particles which are less than approximately 30.

The amount by weight of petrolatum to be added to a mixture of 9 g of particles and 7 g of paste-forming oil in order to produce complete wetting of the powders and a fluid paste respectively is called the wetting point and the flow point respectively of the incorporated particles.

Incorporation of the $TiO_2$ particles is understood to mean the operation which consists in predispersing, by milling, the said particles in a choice of oils and/or of esters and/or of fatty alcohols and/or of ethers with hyperdispersing qualities, so that, after milling the particles and the oils and/or the esters and/or the fatty alcohols and/or the ethers in a triple roll mill or bead mill, a stable white paste is obtained which can be directly included in the industrial process. Incorporation prevents any reagglomeration of the particles which may be responsible for the fall in the photoprotection on the skin of the finished product.

The particles, thus predispersed in this mixture of oils and/or of esters and/or of fatty alcohols and/or of ethers, without an emulsifying agent, change from the cake and agglomerate state (of more than 100 microns) to an ideal monodispersed and monocrystalline form (15 to 30 nm).

As regards the $TiO_2$, this ready-for-use paste for the industrial process is different from commercial suspensions and titanium oxide powders, such as TioVeil (Tioxyde): the white paste is obtained without addition of subsidiary surface-active compounds and of organic compounds.

The incorporation of the ZnO particles is of the same nature as that of $TiO_2$ particles.

It may also be possible to employ zinc oxide particles, such as, for example, those of Spectraveil type, sold by Tioxyde, without ever combining it with TIOVEIL (TIOXYDE), an acicular titanium oxide suspension.

The combination of the two oxides incorporated in oils and/or esters and/or fatty alcohols and/or ethers in accordance with the invention results in a synergic effect on the protection factor, whereas the same combination, without incorporation, does not give rise to this synergy.

Advantageously, the titanium oxide particles exhibit a size of less than or equal to 20±5 nm and the zinc oxide particles a size of greater than or equal to 60±5 nm.

Use may be made, in particular, of $TiO_2$ crystals of rutile type, with a prismatic and non-acicular morphology, for example:

T 805, sold by Degussa (alkylsilane treated) and
  MT 100T, sold by Tayca (aluminum hydroxide and stearic acid coated).

Use may be made, as ZnO particles, of in particular ultrafine particles of powdered zinc oxide, of the Z-dimension and Z-dimension HP1 (sunsmart) or neutral zinc (H & H) type or optionally of an oily suspension of Spectraveil (TIOXYDE) zinc oxide.

The titanium oxide particles preferably exhibit a mean size of 20 nm and the zinc oxide particles a mean size of 60 nm.

According to an advantageous embodiment of the present invention, the paste-forming oils and/or esters and/or fatty alcohols and/or ethers are selected from the group comprising decyl oleate, a $C_{12-15}$ alkyl benzoate, octyl dodecanol, octyl dodecyl neopentanoate, glyceryl oleate and propylene glycol, propylene glycol dioctanoate, capric/caprylic triglycerides, cetearyl octanoate, octyl palmitate, isoarachidyl neopentanoate, dioctyl maleate, dicapryl ether and their mixtures.

The choice will preferably be made to incorporate the titanium oxide particles in a mixture of decyl oleate and of $C_{12-15}$ alkyl benzoate and the zinc oxide particles in capric/caprylic triglycerides.

For example, 50% by weight of $TiO_2$ particles, 30% by weight of Finsolv TN and 20% by weight of Cetiol V (HENKEL) will be mixed.

Advantageously, the titanium oxide is present in the incorporation product at a relative concentration by weight of between 20 and 60% and in the final formulation of at most 25%.

More advantageously still, the zinc oxide is present in the incorporation product at a relative concentration by weight of between 20 and 60%. The final amount in the formulation will be less than 30%.

According to another preferred embodiment of the composition according to the invention, the latter additionally contains pigmental iron oxide particles with a size of 1 to 10 µm or in nanometer-range form of Nassy Cat type from LACHI Inc. (U.S.A.) <50 nm, their relative proportion by weight being between 0.1 and 3%.

The addition of iron oxide has the effect of coloring the formula in the highest factors (PF 30; 40; 50) by introducing yellow and red color in order to render transparent the product spread over the skin and not to have whiteness incompatible with the use, as well as strongly to protect in the I.R. region in particular.

The method for manufacturing a sunscreen composition according to the invention contains a preliminary stage consisting in:

incorporating titanium oxide particles in at least one paste-forming oil and/or ester and/or fatty alcohol and/or ether, in order to obtain incorporated titanium oxide particles, and/or incorporating zinc oxide particles in at least one paste-forming oil and/or ester and/or fatty alcohol and/or ether, in order to obtain incorporated zinc oxide particles, optionally mixing the incorporated titanium oxide particles and the incorporated zinc oxide particles, in order to obtain a paste intended to be incorporated in the said composition.

To obtain incorporated titanium oxide particles, it will be possible, for example, to use dry titanium oxide particles, to incorporate them in an oil and/or an ester and/or a fatty alcohol and/or an ether, to roughly mix the entire combination and to pass it once to three times through a roll mill. The incorporated titanium oxide particles are provided, in this case, in the form of a white, homogeneous and glossy paste.

To obtain incorporated zinc oxide particles, it will be possible to proceed in an analogous way.

According to a preferred embodiment of the method according to the invention, the oil and/or the ester and/or the fatty alcohol and/or the ether for incorporating the titanium oxide particles and the oil and/or the ester and/or the fatty alcohol and/or the ether for incorporating the zinc oxide particles are selected independently of one another, in order to obtain:

a wetting point for the incorporated titanium oxide particles and a wetting point for the incorporated zinc oxide particles which are less than approximately 5, and a flow point for the incorporated titanium oxide particles and a flow point for the incorporated zinc oxide particles which are less than approximately 30.

The composition is advantageously provided in the form of a water-in-oil emulsion, in particular a water-in-oil emulsion in which the oil is silicone-based.

It will be possible to add gelling derivatives of inorganic origin of the group of the Montmorillonites of the Bentone type (38;34) (Quaternium 14, 18 Hectorite) or aerosil [sic] (Degussa, for example Aerosil R 972), which, judiciously introduced during the industrial process, make it possible to optimize the stability of the product. Moreover, they strongly potentiate the solar protection in the highest protection factors and stabilize the protection factor with time.

The composition according to the invention is introduced in a vehicle. It acts as dispersing diluent and transporter of photoprotective materials (metal oxides+inorganic gelling agents) recorded above and it must facilitate their distribution over the human skin while having regard for the microcrystalline dispersion.

This vehicle is in this instance, essentially, with a continuous lipophilic phase, emulsion or anhydrous excipient.

The composition according to the invention can be provided in the form of a suspension or of a dispersion in solvents or fatty substances, in the form of an emulsion, such as a cream or a milk, in the form of an ointment, of a gel or of an anhydrous or non-anhydrous solid compound or be packaged as an aerosol and be provided in the form of a foam.

It can contain the adjuvants usual in this type of composition, such as thickeners, softeners, moisturizers, surfactants, preservatives, sequestrants, antioxidants, antifoaming agents, oils, waxes, lanolin, fragrances, propellants, dyes, vitamins or any other ingredient commonly used.

In the case of a composition packaged as an aerosol, use is made of conventional propellants, such as alkanes, fluoroalkanes and chlorofluoroalkanes, dimethyl ether or nitrous oxide.

Mention may be made, among the main adjuvants which can be present in the compositions of the invention, of solvents, such as water, lower monoalcohols or polyols containing 1 to 6 carbon atoms or their mixtures, monoalcohols or polyols, ethanol, isopropanol, propylene glycol, glycerol and sorbitol; mention may also be made of fatty substances, such as mineral, animal, vegetable or synthetic oils or waxes, fatty acids, esters of fatty acids, such as triglycerides of fatty acids having from 6 to 12 carbon atoms, fatty alcohols, petrolatum, paraffin wax, lanolin, hydrogenated lanolin, acetylated lanolin or silicone oil.

However, use may also be made of the powders talc, various earths, kaolins, starch, plant or synthetic gums, nylon, smectites and derivatives, polyacrylate and derivatives, optionally modified magnesium or aluminum silicates, xanthan and derivatives, carboxyvinyl polymer and derivatives or alternatively preservatives, such as parabens for example, antioxidants, such as B.H.T. for example, fragrances, odor concealers, various active extracts or dyes.

It will be possible to produce an emulsion of the water-in-oil type. It contains an aqueous phase, a fatty phase and an emulsifying system.

In this type of emulsion, the concentration of emulsifying system is between 4 and 35% by weight with respect to the total weight of the emulsion; the fatty phase is present in proportions of between 20 and 60% by weight and the aqueous phase in proportions of between 20 and 70% by weight with respect to the total weight of the emulsion. The emulsifiers are those commonly used in this type of emulsion.

The fatty phase can also contain silicone oils which are soluble in the other oils, such as dimethylpolysiloxane, methyl phenyl polysiloxane and silicone-glycol copolymers, fatty acids and fatty alcohols.

With a view to promoting retention of the oils, it is also possible to use waxes, such as carnauba wax, candelilla wax, beeswax, microcrystalline wax, ozokerite or oleates, myristates, linoleates and stearates of Ca, Mg and Al.

The emulsions of the water-in-oil type can be provided in the form of sticks. In this case, the concentration of the aqueous phase in the emulsion is generally between 5 and 70% by weight with respect to the total weight of the emulsion.

These water-in-oil emulsions are generally prepared by introducing the fatty phase and the emulsifier into a manufacturing vessel. The mixture is heated to a temperature of 70–75° C. The oil-soluble ingredients are then added, followed by the addition, with stirring, of the water, brought beforehand to the same temperature, the water-soluble ingredients having been dissolved beforehand in this water; the mixture is stirred until an emulsion is obtained which has the desired fineness and then the emulsion is allowed to cool to room temperature, optionally with slow stirring.

The fatty gels comprise an oil or wax and a thickener, such as silica. The oil/alcohol or water/alcohol gels comprise one or more lower alcohols or polyols, such as ethanol, propylene glycol or glycerol, and a thickener, such as silica, cellulose derivatives, polyacrylic acid derivatives, guar gum, locust bean gum and xanthan gum, in the presence of oil or of water respectively.

The sticks and other solid anhydrous forms are composed of fatty substances, such as natural or synthetic waxes and oils, fatty alcohols, fatty acid esters and lanolin.

As regards the water-in-silicone emulsions, they can in particular be formulated based:

on silicone emulsifiers resulting from high molecular weight polymers, on dimethyl polysiloxane polymer with polyoxyethylene and/or polyoxypropylene chains having a molecular weight of 10,000 to 50,000.

The dimethyl polysiloxane polymer is often dispersed in volatile silicone. This dispersion comprises, for example, from 1 to 20% by volume of polymer and from 80 to 99% of volatile silicone.

Mention may be made, among these emulsifiers, of Dow 322 5C, Q2 5200 and their derivatives, for example.

Among another family of silicone emulsifiers, polyalkyl polyether polysiloxanes can be employed, for example the copolyolcetyl dimethicone (Abil EM 90) and its derivatives (Abil WE 09 and Abil WS 08) (GOLDSCHMIDT), alone or in combination with a nonionic water/oil emulsifier of polyglycerol ester type.

The composition can comprise, in addition, photoprotective agents, antioxidants and agents for combating free radicals, and other adjuvants.

Mention will be made, as antioxidants and agents for combating free radicals, of, for example: vitamin E and its acetates, vitamin A and its derivatives, β-carotene, retinol, vitamin C and its derivatives, glutathione, selenium, various trace elements, B.H.T., B.H.A., flavonoids and polyphenols of plant origin for example, or melanin and precursors of human, plant, animal or biotechnological origin.

Mention will furthermore be made, as adjuvants, of:

all vegetable oils which can be of advantage to the sun formulation by absorption of UV radiation (sesame, olive, grapeseed, coconut, and the like), all film-forming compounds which make possible good persistence to water and to sweat of the product with time (P.V.P. derivatives, Pemulen and derivatives (Goodrich), silicone wax, water-persistent silicone of DOW 593 type; Antaron (WP660; V 220); Gantrez E 542S or cellulose derivatives).

The compositions in accordance with the invention can be useful in cosmetics for protecting the skin against the short- or long-term effects of UV A and UV B solar radiation.

They can also be useful in the manufacture of medicaments intended to be used in dermatological treatments of complaints such as Benign Estival Photodermatosis (B.E.P.).

I—Incorporation

1—Method

The manner of choosing the oil or the ester or the fatty alcohol or the ether for incorporating the titanium oxide particles, by measuring the wetting point and the flow point, is explained hereinbelow.

Several paste-forming oils or esters or fatty alcohols or ethers are chosen and the points in question are evaluated for each of them or their mixtures.

To do this, 9 g of titanium oxide particles and 7 g of the oil or of the ester in question are used. The amount of petrolatum to be added (x grams) for the determination of the points is reported in Table I below.

The following will be taken as reference:

for the wetting point, 15 g of petrolatum, for the flow point, 60 g of petrolatum.

TABLE I

| Liquid petrolatums g $TiO_2$ | $C_{12-15}$ alkyl benzoate | Octyl dodecyl neopentanoate | Glyceryl oleate propylene glycol | Propylene glycol dioctanoate | Octyl dodecanol | Capric/caprylic triglyceride |
|---|---|---|---|---|---|---|
| Wetting point Coated $TiO_2$ | 2.63 | 1.73 | 2.63 | 2.38 | 2.24 | 3.91 |
| Flow point Coated $TiO_2$ | 30.94 | 23.37 | 26.5 | 30.33 | 30.38 | 31.8 |

2—Advantage of the incorporation
a) Advantage of the mechanical oily dispersion and of the choice of the ester for incorporating $TiO_2$ The sun protection factor of compositions based on $TiO_2$ particles as a function of the nature of the incorporation is measured. The same factor for B+A protection against sunstroke for non-incorporated particles is also measured.

TABLE II

| Grade of $TiO_2$ | P.F. (B + A) at 5% | P.F. (B + A) at 10% |
|---|---|---|
| $TiO_2$, coated | 5 | 10 |
| $TiO_2$, incorporated liquid petrolatum | 5 | 10 |
| $TiO_2$, Incorporation 1 | 7 | 14 |
| $TiO_2$, Incorporation 2 | 10 | 20 |

Incorporation 1: octyldodecanol
Incorporation 2: decyl oleate

Incorporation 1: octyldodecanol
Incorporation 2: decyl oleate

These measurements show the advantage of mechanically dispersing the $TiO_2$ in a chosen lipid. The protection is greater than that provided by non-incorporated particles.

Moreover, differences in dispersion and thus in photoprotection between the incorporations are observed. Liquid petrolatum is ineffective, fatty alcohol is fairly effective and decyl oleate doubles the photoprotection.

b) Advantage of the dispersion of the metal oxides

The protection factor of various compositions as a function of the incorporation of the $TiO_2$ and ZnO particles by different incorporations is measured

| | | |
|---|---|---|
| −12.5% $TiO_2$ + 1.2% ZnO nondispersed | → | PF 15 |
| −12.5% $TiO_2$ + 1.2% ZnO in Incorporation 1 | → | PF 35 |
| −12.5% $TiO_2$ + 1.2% ZnO in Incorporation 2 | → | PF 70 | in Incorporation 2 c) Effect of the amount of $TiO_2$ particles with Incorporation 2

The protection factor of various compositions as a function of the amount of the $TiO_2$ particles incorporated in decyl oleate is again measured

| | | |
|---|---|---|
| −8% $TiO_2$ + 1.2% ZnO | → | PF 30 |
| −10% $TiO_2$ + 1.2% ZnO | → | PF 36 |
| −12.5% $TiO_2$ + 1.2% ZnO | → | PF 70 | d) Effect of the amount of ZnO

The protection factor of various compositions as a function of the amount of the ZnO particles incorporated in Incorporation 2 is once more measured

| | | |
|---|---|---|
| −10.5% $TiO_2$ + 1.2% ZnO (Incorporation 2) | → | PF 36.4 |
| −10.5% $TiO_2$ + 2.4% ZnO (Incorporation 2) | → | PF 50 | e) Advantage of $Fe_2O_3$

The advantage of the presence of iron oxide is the coloring of the skin, of compositions containing high doses of metal oxides ($TiO_2$ and ZnO), in order to make possible immediate transparency after application to the skin, for high-factor products.

In order to measure the color of the skin, a colorimetric test (L, a, b) is carried out after application to the bare skin of 2 formulae, with and without iron oxides

| | |
|---|---|
| 10.5% $TiO_2$+2.4% ZnO | Formula A |
| 10.5% $TiO_2$+2.4% ZnO+2% | Formula B | of a mixture of iron oxides

It appears that the formula B gives the skin a natural color similar to untreated skin.

f) Advantage of the gelling inorganics

The sun protection factor of a composition containing a gelling agent is calculated; the results are as follows:

| | | |
|---|---|---|
| Formula with 0.3% of Bentone 38 | → | PF 44 |
| Formula with 0.8% of Bentone 38 | → | PF 55 | g) UV A Protection

The UV A protection was calculated by the P.P.D. or "Permanent Pigmentation Darkening" method, the inhibition of immediate tanning by short- and long-wave UV A radiation of a skin treated with the photoprotective formula being evaluated against the tanning of a bare skin, with the tanning being read at 2 hours.

Irradiation is carried out with a Robertson Berger lamp, WG 335 and UG 11 screened.

h) Advantage of the ZnO and incorporated $TiO_2$ combination

The protection factors of formulations containing either $TiO_2$ particles only or ZnO particles only or a mixture of both are measured.

The results are recorded below:

| | | |
|---|---|---|
| −10% $TiO_2$ powder | → | UV A PF 4 |
| −2.4% ZnO | → | UV A PF 2.5 |
| −10% incorporated $TiO_2$/% decyl oleate + 2.4 ZnO | → | UV A PF 10 |

The effect of the amount of each powder on the protection factor is evaluated below:

| | | |
|---|---|---|
| −8% $TiO_2$/decyl oleate + 1.2% ZnO | → | UV A PF 6.5 |
| −10% $TiO_2$/decyl oleate + 1.2% ZnO | → | UV A PF 8.2 |
| −10% $TiO_2$/decyl oleate + 2.4% ZnO | → | UV A PF 10 |

II—Stability with time and according to the method

The procedure for measuring the stability with time of the compositions is as follows:

The formulations based on incorporation or suspension of $TiO_2$+ZnO are stored at a warmth at 40° C. over periods of 3 months. The UV B+A PF at room temperature and then after 1 month and 3 months at 40° C. are calculated.

The results are combined in the following Table III.

TABLE III

| | TO | T, 1 month, 40° C. | T, 3 months, 40° C. |
|---|---|---|---|
| FR 12 15 | 44 ± 5 | 42 ± 5 | — |
| FR 12 35 - LP | 50 ± 5 | — | 49 ± 5 |

It is observed that the compositions according to the invention are particularly stable.

The stability over several years is thus evaluated: 1 month at 40° C. is equivalent to 1 year at room temperature; the incorporation makes it possible to retain the dispersion of the inorganics with time.

The invention can be better understood using the non-limiting examples which follow and which constitute favored embodiments of the composition according to the invention.

EXAMPLES

Examples of formulations of sunscreen compositions according to the invention are set out below. The percentages are percentages by weight.

1—Examples of formulations

| | |
|---|---|
| DOW CORNING 3225 C | 10.00 g |
| DECAMETHYL CYCLOPENTASILOXANE | 1 to 10 g |
| TITANIUM PASTE | 1 to 50 g |
| SPECTRAVEIL MOTG | 0.1 to 20 g |
| WHITE PETROLATUM, GRADE A | 1.000 g |
| BENTONE 38, STERILIZED | 0.1 to 2 g |
| GLYCEROL MONOSTEARATE | 0.1 to 2 g |
| MONOMULS 90L12 | 0.1 to 2 g |
| ALPHA TOCOPHEROL ACETATE | 0.500 g |

-continued

| | |
|---|---|
| NaCl, SUPER, PURIFIED, DESULFATED | 2.000 g |
| KELTROL T.F. | 0.150 g |
| WITCONOL APM | 0.800 g |
| PARAHYDROXY BENZOATES | 0.600 g |
| EUXYL K 400 | 0.100 g |
| GLYCEROL | 8.000 g |
| DISODIUM EDETATE EU PH | 0.200 g |
| PIGMENTAL MIXTURE 17123 | 2.000 g |
| FRAGRANCE | 0.100 g |
| AEROSIL R972 COLLOIDAL SILICA | 0.100 to 1 g |
| BUTYL HYDROXY TOLUENE | 0.0100 g |
| THERMAL WATER FROM AVENE q.s. for | 100.00 g |

Note:
MONOMULS 90L12 is glycerol monolaurate (HENKEL)
KELTROL T.F. is xanthan gum (KELCO)
WITCONOL APM is DPO 3 myrestyl ether (WITCO)
EUXYL K 400 is dibromo dicyanobutane phenoxyethanol (CALGON)
DISODIUM EDETATE EU PH is 2 Na EDTA (BASF)

Note:

MONOMULS 90L12 is glycerol monolaurate (HENKEL)

KELTROL T.F. is xanthan gum (KELCO)

WITCONOL APM is DPO 3 myrestyl ether (WITCO)

EUXYL K 400 is dibromo dicyanobutane phenoxyethanol (CALGON)

DISODIUM EDETATE EU PH is 2 Na EDTA (BASF)

| INORGANIC SUNCREAM | |
|---|---|
| | Percentages |
| ABIL WE 09 | 4 |
| ELFACOS ST 37 | 0.6 |
| LIQUID PARAFFIN | 1 to 10.0 |
| TiO$_2$ PASTE | 1 to 70 |
| Na Cl | 0.7 |
| PRESERVATIVES | q.s for 100 |
| ZINC OXIDE, COATED | 1 to 25 |
| HYDROXYPROPYLTRIMONIUM GUAR | 0.7 |
| WATER | q.s. for 100 |
| BENTONE 38 - Quaternium 18 | 0.1 to 5 |
| AEROSIL R 972 | 0.1 to 5 |

ABIL WE 09= Cetyl dimethicone Copolyol (GOLDSCHMIDT) (and) polyglyceryl 4 isostearate (and) hexyl laurate
ELFACOS ST 37 (AKZO)= PEG 22/Dodecyl glycol copolymers
Bentone 38= Quaternium 18 - Hectorite (Rheox)

ABIL WE 09 =Cetyl dimethicone Copolyol (GOLDSCHMIDT) (and) polyglyceryl 4 isostearate (and) hexyl laurate ELFACOS ST 37 (AKZO)=PEG 22/Dodecyl glycol copolymers Bentone 38=Quaternium 18—Hectorite (Rhéox)

| INORGANIC and ORGANIC W/O SUNCREAM | |
|---|---|
| | Percentages |
| HOSTERACIN W/O | 10 to 15 |
| TiO$_2$ PASTE | 1 to 70 |
| ANTARON WP 660 | 0.1 to 3 |
| ZnO, COATED AND INCORPORATED TO 50% | 1 to 50 |
| PRESERVATIVES | q.s. for [sic] |
| CINNAMATE | 0 to 10 |
| DIBENZOYLMETHANE | 0 to 4 |
| WATER | q.s. for 100 |

| INORGANIC and ORGANIC W/O SUNCREAM | |
|---|---|
| | Percentages |
| GAMMA ORYZANOL | 0.2 |
| BENTONE 38 | 0.1 to 5 |
| AEROSIL R 972 | 0.1 to 6 |

HOSTERACIN W/O (HOECHST): polyglyceryl 2 sesquiisostearate (and) beeswax (and) inorganic Al (and) magnesium stearate (and) aluminum stearate [sic].
ANTARON WP 660 (I.S.P.): Tricantanyl Polyvinylpyrrolidone [sic]

HOSTERACIN W/O (HOECHST): polyglyceryl 2 sesquiisostearate (and) beeswax (and) inorganic Al (and) magnesium stearate (and) aluminum stearate [sic].

ANTARON WP 660 (I.S.P.): Tricantanyl Polyvinylpyrrolidone [sic]

| INORGANIC AND ORGANIC HIGH SUNCREAM | |
|---|---|
| | Percentages |
| DOW 3225C | 5 to 15 |
| TiO$_2$ paste in FINSOLV TN and CETIOL VA 50% | 0.1 to 60 |
| ZnO, COATED, POWDERED | 0.1 to 25 |
| CINNAMATE | 0 to 10 |
| DIBENZOYLMETHANE | 0 to 4 |
| MONOMULS 90 L 12 | 0.1 to 2 |
| GLYCEROL MONOSTEARTE | 0.1 to 2 |
| OZOKERITE | 0.1 to 3 |
| TOCOPHEROL ACETATE (Vitamin E) | 0.1 to 1 |
| WITCONOL APM | 0.1 to 1 |
| PRESERVATIVE | q.s. for 100 |
| GLYCEROL | 1 to 10 |
| IRON OXIDE MIXTURE | 0.1 to 5 |
| COLLOIDAL SILICA | 0.1 to 5 |
| MONTMORILLONITE | 0.1 to 5 |
| WATER | q.s. for 100 |

MONOMULS 90 L 12: glycerol monolaurate (HENKEL)
WITCONOL APM: PPB3 - ether of myristyl (WITCO)
DOW 3225C: cyclomethicone and dimethicone copolyol MONOMULS 90 L 12: glycerol monolaurate (HENKEL)

WITCONOL APM: PPB3—ether of myristyl (WITCO)

DOW 3225C: cyclomethicone and dimethicone copolyol

| W/SILICONE SUNCREAM | |
|---|---|
| | Percentages |
| ABIL EM 90 | 1 to 5 |
| ABIL WAX 9801 | 0.2 to 6 |
| DOW 345 | 0.1 to 10 |
| TiO$_2$ INCORPORATED TO 30% | 0.1 to 70 |
| ZnO, COATED, POWDER | 0.1 to 25 |
| WATER | q.s. for 100 |
| NaCl | 0.1 to 3 |

ABIL EM 90: cetyl dimethicone copolyol (GOLDSCHMIDT)
ABIL WAX 9801: cetyl dimethicone (GOLDSCHMIDT)
DOW 345: cyclomethicone (DOW CORNING)

ABIL EM 90: cetyl dimethicone copolyol (GOLDSCHMIDT)

ABIL WAX 9801: cetyl dimethicone (GOLDSCHMIDT)

DOW 345: cyclomethicone (DOW CORNING)

W/O SUNCREAM

| | Percentages |
|---|---|
| ISOLAN GI 34 | 1 to 10 |
| TiO$_2$, INCORPORATED TO 50% | 1 to 60 |
| ZnO, AS A 60% SUSPENSION | 1 to 50 |
| DOW 345 | 1 to 10 |
| WHITE PETROLATUM | 1 to 10 |
| WATER | q.s. for 100 |
| GLYCEROL | 1 to 10 |
| NaCl | 0.1 to 2 |

ISOLAN GI 34 (GOLDSCHMIDT): polyglyceryl 4-isostearate.

W/SILICONE OIL MILK

| | Percentages |
|---|---|
| Q2 5200 | 5 to 15 |
| DOW 345 | 1 to 10 |
| TiO$_2$ INCORPORATED TO 20% IN CETIOL V | 1 to 80 |
| ZnO, COATED, POWDERED | 1 to 25 |
| CINNAMATE | 0 to 40 |
| DIBENZOYL METHANE | 0 to 4 |
| ANTORAN V 220 PVP copolymer | 0.1 to 3 |
| BEESWAX | 1 to 4 |
| WATER | q.s. for 100 |
| FRAGRANCE | 0.1 to 1 |
| PRESERVATIVES | q.s. for [sic] |

Q2 5200 (DOW CORNING): laurylmethicone [sic] copolyol.

DENSE W/SILICONE O SUNCREAM

| | Percentages |
|---|---|
| ABIL WE 09 | 0.5 to 5 |
| WATER | 1 |
| CARNAUBA WAX | 1 to 10 |
| HYDROGENATED LANOLIN | 1 to 10 |
| ACETOXYSTEARATE | 1 to 10 |
| TiO$_2$ INCORPORATED to 50% in FINSOLV TN and CETIOL V | 1 to 70 |
| ZnO, COATED | 1 to 25 |
| BENZYLIDENE CAMPHOR | 0 to 8 |
| DIBENZOYL METHANE | 0 to 4 |
| BUTYL HYDROXY TOLUENE | 1 |
| IRON OXIDE, COATED | 0 to 2 |
| BENTONE 34 | 0.1 to 5 |
| AEROSIL | 0.1 to 5 |

ABIL WE 09: cetyl dimethicone copolyol (and) polyglyceril 4 isostearate (and) hexyl laurate (GOLDSCHMIDT).

INORGANIC HIGH PROTECTION SUN MILK

| | Percentages |
|---|---|
| DOW 3225 C | 5 to 15 |
| DECAMETHYL CYCLO PENTASILOXANE | 1 to 10 |
| TITANIUM PASTE AT 45% IN MIGLYOL 812 | 1 to 70 |
| SPECTRAVEIL MOTG | 0.1 to 20 |

INORGANIC HIGH PROTECTION SUN MILK

| | Percentages |
|---|---|
| BENTONE 38 | 0.1 to 5 |
| GLYCEROL MONOSTEARATE | 0.1 to 2 |
| TOCOPHEROL ACETATE | 0.1 to 1 |
| NaCl | 2 |
| PRESERVATIVE | q.s. for 100 |
| GLYCEROL | 1 to 10 |
| EDTA | 0.1 to 0.2 |
| IRON OXIDE MIXTURE | 0.1 to 5 |
| FRAGRANCE | |
| COLLOIDAL SILICA | 0.1 to 5 |
| MINERAL OR DEMINERALIZED WATER | q.s. for 100 |

INORGANIC + ORGANIC SUNCREAM

| | Percentages |
|---|---|
| ABIL WE 09 | 3 |
| TiO$_2$ PASTE | 1 to 70 |
| ZnO, COATED | 1 to 25 |
| CINNAMATE | 0.1 to 10 |
| DIBENZOYL METHANE | 0.1 to 4 |
| OZOKERITE | 1 |
| PRESERVATIVES | q.s. for 100 |
| WATER | q.s. for 100 |
| BENTONE 34 - Quaternium 18 bentonite (. . . ) | 0.1 to 5 |
| AEROSIL R 972 | 0.1 to 5 |

ANHYDROUS COMPACT FOR PROTECTING AND CORRECTING THE COMPLEXION

| | Percentages |
|---|---|
| TiO$_2$ INCORPORATED to 50% (in tridecyl stearate and neopentyl glycol, caprate and dicaprylate and tridecyl trimellitate) | 1 to 70 |
| ZnO, COATED AND INCORPORATED TO 50% | 1 to 50 |
| CINNAMATE | 0 to 10 |
| DIBENZOYL METHANE | 0 to 4 |
| IRON OXIDE | 12.7 |
| ISOSTEARYL NEOPENTANOATE | 5 |
| CARNAUBA WAX | 2 |
| ULTRAMARINE | 1 |
| OZOKERITE | 1 |
| PRESERVATIVES | q.s. for 100 |
| BENTONE 38 - Quaternium 18 - Hectorite | 0.1 to 5 |
| AEROSIL R 972 | 0.1 to 5 |

TOTAL SUNBLOCK STICK

| | Percentages |
|---|---|
| TOCOPHEROL ACETATE | 0.5 |
| CINNAMATE [sic] | 0 to 10 |
| DIBENZOYL METHANE [sic] | 0 to 14 |
| TiO$_2$ INCORPORATED to 40% in FINSOLV TN | 1 to 70 |
| ZnO, coated and incorporated in FINSOLV TN to 50% | 1 to 50 |
| ETHYLHEXYL ACETOXYSTEARATE | 1 to 6 |
| CARNAUBA WAX | 1 to 15 |
| BUTYL HYDROXY TOLUENE | 0.01 |
| FRAGRANCE | 0.1 to 2 |

-continued

TOTAL SUNBLOCK STICK

| | Percentages |
|---|---|
| BENTONE 38 | 0.1 to 5 |
| AEROSIL R 972 | 0.1 to 5 |

We claim:

1. A sunscreen composition comprising a synergic mixture of a first component incorporated in a second component without addition of surface active compounds, wherein said first component is selected from the group consisting of titanium oxide particles, zinc oxide particles and mixtures thereof, and said second component is selected from the group consisting of paste-forming oils, esters, fatty alcohols, ethers and mixtures thereof, said composition having a wetting point for the incorporated titanium oxide particles and a wetting point for the incorporated zinc oxide particles which are less than approximately 5, and a flow point for the incorporated titanium oxide particles and a flow point for the incorporated zinc oxide particles which are less than approximately 30.

2. Sunscreen composition according to claim 1, wherein the titanium oxide particles exhibit a size of less than or equal to 20±5 nm and the zinc oxide particles a size of greater than or equal to 60±5 nm.

3. Sunscreen composition according to claim 1 wherein the titanium oxide particles exhibit a mean size of 20 nm and the zinc oxide particles a mean size of 60 nm.

4. Sunscreen composition according to claim 1 wherein said second component is selected from the group consisting of decyl oleate, a $C_{12-15}$ alkyl benzoate, octyl dodecanol, octyl dodecyl neopentanoate, glyceryl oleate, propylene glycol, propylene glycol dioctanoate, capric/caprylic triglycerides, cetearyl octanoate, octyl palmitate, isoarachidyl neopentanoate, dioctyl maleate, dicapryl ether and mixtures thereof.

5. Sunscreen composition according to claim 1 wherein said first component is a mixture of titanium oxide particles and zinc oxide particles, said second component for incorporating the titanium oxide particles is a mixture of decyl oleate and a $C_{12-15}$ alkyl benzoate, and said second component for incorporating the zinc oxide particles comprises capric/caprylic triglycerides.

6. Sunscreen composition according to claim 1 wherein titanium oxide is present at a relative concentration by weight of between 20 and 60% in the incorporation product and of at most 25% in the finished product.

7. Sunscreen composition according to claim 1 wherein zinc oxide is present at a relative concentration by weight of between 20 and 60% in the incorporation product and of at most 30% in the finished product.

8. Sunscreen composition according to claim 1 further comprising iron oxide particles with a mean size of 1 to 10 μm, their relative proportion by weight being between 0.1 and 3%.

9. A method for manufacturing a sunscreen composition according to claim 1 comprising the steps of:

a) incorporating titanium oxide particles in a second component selected from the group consisting of paste-forming oil, ester, fatty alcohol, ether, and mixtures thereof in order to obtain incorporated titanium oxide particles;

b) incorporating zinc oxide particles in a second component selected from the group consisting of paste-forming oil, ester, fatty alcohol, ether, and mixtures thereof in order to obtain incorporated zinc oxide particles; and then, c) mixing the incorporated titanium oxide particles and the incorporated zinc oxide particles, in order to obtain a paste intended to be incorporated in said composition.

10. The method according to claim 9, wherein said second component for incorporating the titanium oxide particles and said second component for incorporating the zinc oxide particles are selected independently of one another, in order to obtain:

a wetting point for the incorporated titanium oxide particles and a wetting point for the incorporated zinc oxide particles which are less than approximately 5, and a flow point for the incorporated titanium oxide particles and a flow point for the incorporated zinc oxide particles which are less than approximately 30.

11. Method according to either one of claims 9 and 10, wherein the composition is a water-in-oil emulsion.

12. Cosmetic use of a sunscreen composition according to claim 1 or 2, for protecting the skin against all the short- or long-term effects of UV B and UV A solar radiation.

13. Use of a sunscreen composition according to claim 1 or 2, for the manufacture of medicaments intended to be used in dermatological treatments of complaints such as Benign Estival Photodermatosis (B.E.P.).

14. The method of claim 11 wherein the oil is silicone-based.

15. A method for manufacturing a sunscreen composition according to claim 1 comprising the step of incorporating titanium oxide particles in a second component selected from the group consisting of paste-forming oils, esters, fatty alcohols, ethers and mixtures thereof in order to obtain incorporated titanium oxide particles, said incorporated particles forming a paste intended to be incorporated in said composition.

16. The method of claim 15 wherein said composition is a water-in-oil emulsion.

17. The method of claim 16 wherein the oil is silicone-based.

18. A method for manufacturing a sunscreen composition according to claim 1 comprising the step of incorporating zinc oxide particles in a second component selected from the group consisting of paste-forming oils, esters, fatty alcohols, ethers and mixtures thereof in order to obtain incorporated zinc oxide particles, said incorporated particles forming a paste intended to be incorporated in said composition.

19. The method of claim 18 wherein said composition is a water-in-oil emulsion.

20. The method of claim 19 wherein the oil is silicone-based.

* * * * *